United States Patent
Yoshikawa et al.

Patent Number: 5,374,764
Date of Patent: Dec. 20, 1994

[54] 5-AMINOSULFONANILIDE COMPOUNDS

[75] Inventors: Kensei Yoshikawa, Urawa; Shiuji Saito, Okegawa; Yohichi Shimazaki; Mariko Kashiwa, both of Tokyo; Katsuo Hatayama, Ohmiya, all of Japan

[73] Assignee: Taisho Pharmaceutical Co., Ltd., Japan

[21] Appl. No.: 190,123

[22] PCT Filed: Aug. 7, 1992

[86] PCT No.: PCT/JP92/01013

§ 371 Date: Feb. 3, 1994

§ 102(e) Date: Feb. 3, 1994

[87] PCT Pub. No.: WO93/03008

PCT Pub. Date: Feb. 18, 1993

[30] Foreign Application Priority Data

Aug. 8, 1991 [JP] Japan .................. 3-285360
Jan. 28, 1992 [JP] Japan .................. 4-012492
Mar. 9, 1992 [JP] Japan .................. 4-050371

[51] Int. Cl.$^5$ .......................... C07C 311/02
[52] U.S. Cl. .......................... 560/13; 564/99
[58] Field of Search .................. 564/99; 560/13

[56] References Cited

U.S. PATENT DOCUMENTS 3,840,597 10/1974 Moore et al. .
3,906,024 9/1975 Moore et al. .
4,866,091 9/1989 Matsuo .
4,885,367 12/1989 Yoshikawa et al. ............ 546/216

FOREIGN PATENT DOCUMENTS 61-10548 1/1986 Japan .
222260 7/1988 Japan .
2300122 5/1989 Japan .

OTHER PUBLICATIONS

Chemical Abstract 114: 192589; JP 02300122 1990.

Primary Examiner—José G. Dees
Assistant Examiner—Samuel Barts
Attorney, Agent, or Firm—Lorusso & Loud

[57] ABSTRACT

5-Aminosulfonanilide compounds represented by the formula:

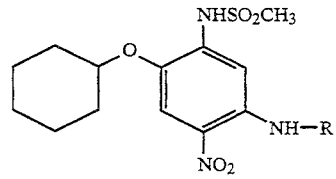

(wherein R is a hydrogen atom, a formyl group, an acetyl group, a propionyl group, an n-butyryl group, an n-valeryl group, an ethoxyoxalyl group, an n-propoxyoxalyl group, a methoxycarbonylacetyl group or a 3-ethoxycarbonylpropionyl group) have potent anti-inflammatory, antipyretic, analgesic and anti-allergic actions, and therefore they are useful as anti-inflammatory, antipyretic, analgesic and anti-allergic agents.

1 Claim, No Drawings

5-AMINOSULFONANILIDE COMPOUNDS

BACKGROUND ART

The present inventors have already disclosed useful sulfonanilide compounds having anti-inflammatory, antipyretic, analgesic and anti-allergic actions as described in the specification of U.S. Pat. No. 4,885,369.

DISCLOSURE OF THE INVENTION

For the purpose of providing compounds which have higher anti-inflammatory, antipyretic, analgesic and anti-allergic actions, the present inventors have synthesized various 5-aminosulfonanilide compounds, and have studied the pharmacological actions thereof. As a result, it has been found that 5-aminosulfonanilide compounds represented by Formula (I):

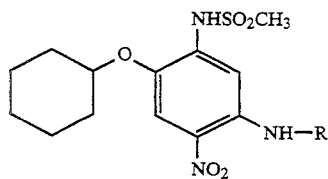

(wherein R is a hydrogen atom, a formyl group, an acetyl group, a propionyl group, an n-butyryl group, an n-valeryl group, an ethoxyoxalyl group, an n-propoxyoxalyl group, a methoxycarbonylacetyl group or a 3-ethoxycarbonylpropionyl group) have potent anti-inflammatory, antipyretic, analgesic and anti-allergic actions, and thus the present invention has been accomplished. That is, the present invention is the compounds of Formula (I) useful as anti-inflammatory, antipyretic, analgesic and anti-allergic agents.

The compounds of Formula (I) of the present invention can be prepared, for example, by a method as shown below.

(1) The compounds of Formula (I) wherein R is other than a hydrogen atom can be prepared from 2-fluoro-5-nitroaniline as a starting material as follows:

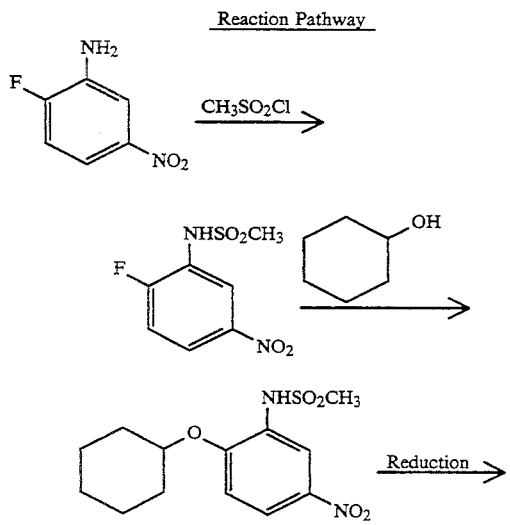

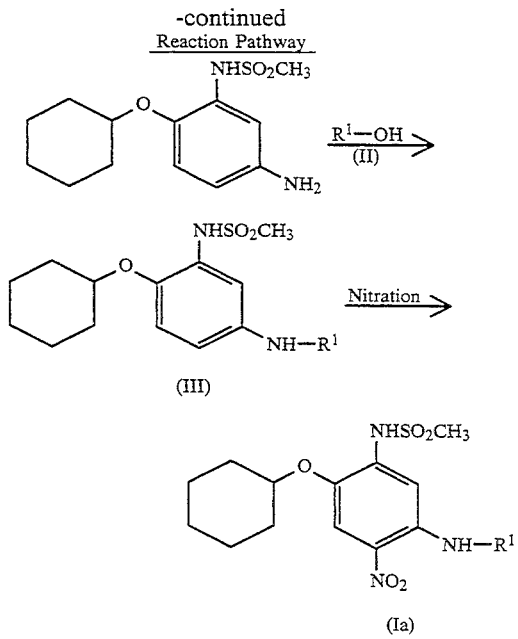

(wherein $R^1$ is R other than a hydrogen atom).

(a) First, the amino group of 2-fluoro-5-nitroaniline is sulfonylated by using methanesulfonyl chloride to give N-(2-fluoro-5-nitrophenyl)methanesulfonamide.

This reaction may be preferably carried out in the presence of a base such as, for example, an inorganic base (e.g. lithium hydroxide, sodium hydroxide, potassium hydroxide, sodium carbonate, potassium carbonate, sodium bicarbonate or potassium bicarbonate), or an organic base (e.g. triethylamine, tri-n-butylamine, 1,5-diazabicyclo[4.3.0]-5-nonene, 1,8-diazabicyclo[5.4.0]-7-undecene, 4-methylmorpholine, 1-methylpiperidine, pyridine or N,N-dimethylaminopyridine).

Furthermore, this reaction is usually carried out in a solvent such as, for example, dichloromethane, chloroform, ethyl acetate, dioxane, tetrahydrofuran, ethyl ether, benzene, toluene, xylene, acetone, acetonitrile, water, pyridine, N,N-dimethylformamide or dimethyl sulfoxide.

(b) Then, N-(2-fluoro-5-nitrophenyl)methanesulfonamide and cyclohexanol are subjected to etherification in the presence of a base to give N-(2-cyclohexyloxy-5-nitrophenyl)methanesulfonamide.

Examples of the base in the reaction include alkali metal hydroxides (e.g. lithium hydroxide, sodium hydroxide and potassium hydroxide), alkali metal carbonates (e.g. sodium carbonate and potassium carbonate), alkali metal bicarbonates (sodium bicarbonate and potassium bicarbonate), alkali metal hydrides (e.g. sodium hydride and potassium hydride), inorganic bases (e.g. sodium and sodium amide) and organic bases (e.g. triethylamine, tri-n-butylamine, 1,5-diazabicyclo[4.3.0]-5-nonene, 1,8-diazabicyclo[5.4.0]-7-undecene, pyridine and N,N-dimethylaminopyridine).

This reaction may be carried out in the absence or presence of a solvent which is arbitrarily chosen, for example, dioxane, tetrahydrofuran, ethyl ether, petroleum ether, n-hexane, cyclohexane, benzene, toluene, xylene, chlorobenzene, pyridine, N,N-dimethylformamide, dimethyl sulfoxide, dichloromethane or chloroform. Furthermore, the reaction can be accelerated by adding sodium iodide, tris[2-(2-methoxyethoxy)ethyl]amine, a quaternary ammonium salt (e.g. tetra-n-butylammonium chloride, tetra-n-butylammonium bromide, benzyltriethylammonium chloride, benzyltriethylammonium bromide and tricaprylylmethylammonium chloride) or a crown ether (e.g. 18-crown-6 ether).

(c) Then, the nitro group of N-(2-cyclohexyloxy-5-nitrophenyl)methanesulfonamide is reduced to give N-(5-amino-2-cyclohexyloxyphenyl)methanesulfonamide.

This reaction may be an ordinary reduction by which a nitro group leads to an amino group, for example, a catalytic reduction using palladium-carbon, Raney nickel or platinum as a catalyst, a reduction using iron or tin, a reduction using sodium sulfideammonium chloride or a reduction using sodium borohydride or lithium aluminium hydride. The solvent to be used in the reaction can be arbitrarily chosen depending on the reduction. Generally, for example, alcohols (e.g. methanol, ethanol and n-propanol), water, acetic acid, ethyl acetate, dioxane, tetrahydrofuran or acetonitrile can be used as the solvent.

(d) Subsequently, the amino group of N-(5-amino-2-cyclohexyloxyphenyl)methanesulfonamide obtained above is converted into an amide by a compound of Formula (II) $R^1$—OH (wherein $R^1$ is as defined above) or a reactive derivative thereof (e.g. an acid anhydride or an acid halide) to give a compound of Formula (III).

When a carboxylic acid of Formula (II) is used, the reaction is preferably carried out in the presence of a condensing agent such as N,N'-dicyclohexylcarbodiimide, 1,1'-carbodiimidazole, methanesulfonyl chloride or ethyl chloroformate. When the reactive derivative (e.g. an acid anhydride or an acid halide) is used, the reaction is preferably carried out in the presence of a base such as, for example, an inorganic base (e.g. lithium hydroxide, sodium hydroxide, potassium hydroxide, sodium carbonate, potassium carbonate, sodium bicarbonate or potassium bicarbonate) or an organic base (e.g. triethylamine, tri-n-butylamine, 1,5-diazabicyclo[4.3.0]-5-nonene, 1,8-diazabicyclo[5.4.0]-7-undecene, 4-methylmorpholine, 1-methylpiperidine, pyridine and N,N-dimethylaminopyridine).

Generally, this reaction is carried out in the presence of a solvent such as, for example, dichloromethane, chloroform, ethyl acetate, dioxane, tetrahydrofuran, ethyl ether, benzene, toluene, xylene, acetone, acetonitrile, water, pyridine, N,N-dimethylformamide and dimethyl sulfoxide.

(e) Finally, the compound of Formula (III) is nitrated by a nitrating agent such as nitric acid or nitrate to give a compound of the present invention wherein R is other than a hydrogen atom [compound of Formula (Ia)].

Examples of the nitrating agent to be used in the nitration include nitric acid, sodium nitrate, potassium nitrate, ferric nitrate and urea nitrate. The solvent to be used in the reaction is arbitrarily chosen depending on the nitrating agent to be used, for example, acetic acid, acetic anhydride, trifluoroacetic acid, sulfuric acid, dichloromethane, chloroform, benzene, dioxane or ethanol.

(2) N-(5-Amino-2-cyclohexyloxy-4-nitrophenyl)methanesulfonamide which is a compound of the present invention of Formula (I) wherein R is a hydrogen atom can be obtained by hydrolyzing the compound of Formula (Ia)

The hydrolysis in this reaction may be an ordinary hydrolysis of an amide under the basic or acidic condition, for example, a hydrolysis using lithium hydroxide, sodium hydroxide, potassium hydroxide, sodium carbonate, potassium carbonate, sodium methoxide, sodium ethoxide or potassium t-butoxide for the basic condition, or a hydrolysis using hydrochloric acid, hydrobromic acid or sulfuric acid for the acidic condition.

Examples of the solvent to be used in the reaction include water, methanol, ethanol, propanol, t-butanol, tetrahydrofuran, dioxane, benzene, toluene, xylene, chlorobenzene, N,N-dimethylformamide, dimethyl sulfoxide, formic acid and acetic acid, but it is preferable that the solvent is appropriately chosen depending on the condition of the hydrolysis.

The compounds of the present invention can be administered orally or parenterally in the conventional dosage forms such as, for example, tablets, powders, granules, powders, capsules, solutions, emulsions, suspensions and injections, all of which can be prepared by ordinary practices. The dose used for humans as an anti-inflammatory, antipyretic, analgesic or anti-allergic agent is different depending on the age, body weight, symptoms, route of administration and frequency of administration, but it is usually from 5 to 1000 mg per day.

BEST MODE FOR CARRYING OUT THE INVENTION

The present invention is illustrated in more detail by the following examples and experiments.

EXAMPLE 1

(1) To 1300 ml of a pyridine solution containing 204.0 g of 2-fluoro-5-nitroaniline was added 165.0 g of methanesulfonyl chloride under ice cooling, followed by stirring at room temperature for 24 hours. To the reaction solution was added 3000 ml of water, and the precipitate was collected by filtration, air-dried overnight and recrystallized from ethanol to give 230.0 g of N-(2-fluoro-5-nitrophenyl)methanesulfonamide as colorless needles.
m.p. 128°–129° C.

(2) To 2000 ml of a chlorobenzene solution containing 52.8 g of 60% sodium hydride were successively added 128.0 g of cyclohexanol and 8 ml of tris[2-(2-methoxyethoxy)ethyl]amine at room temperature, and then after stirring for 30 minutes, 100.0 g of N-(2-fluoro-5-nitrophenyl)methanesulfonamide was added under ice cooling, followed by stirring for 19 hours. The reaction solution, after addition of 1500 ml of 3N hydrochloric acid, was extracted with dichloromethane, and the organic layer was successively washed with water and a saturated aqueous sodium chloride solution, and dried over anhydrous magnesium sulfate. After evaporation of the solvent, the residue was recrystallized from ethanol to give 98.5 g of N-(2-cyclohexyloxy-5-nitrophenyl)methanesulfonamide as yellow plates.
m.p. 105°–106.5° C.

(3) To 100 ml of an aqueous solution containing 5.0 g of ammonium chloride were added 98.0 g of N-(2-cyclohexyloxy-5-nitrophenyl)methanesulfonamide and 78.0 g of an iron powder with heating at 80° C. with stirring, followed by stirring for 2 hours. The reaction solution was cooled back to room temperature, and then ethyl acetate and water were added thereto. After extraction, the organic layer was successively washed with water and a saturated aqueous sodium chloride solution, and dried over anhydrous magnesium sulfate. After evaporation of the solvent, the residue was recrystallized from ethanol to give 71.7 g of N-(5-amino-2-cyclohexyloxyphenyl)methanesulfonamide as colorless prisms.

m.p. 151.5°–153.5° C.

(4) To 105 ml of a pyridine solution containing 20.0 g of N-(5-amino-2-cyclohexyloxyphenyl)methanesulfonamide was added 10.2 g of n-valeryl chloride under ice cooling, followed by stirring at room temperature for 30 minutes. The reaction solution, after addition of water, was extracted with ethyl acetate, and then the organic layer was successively washed with water, 3N hydrochloric acid, water and a saturated aqueous sodium chloride solution, and dried over anhydrous magnesium sulfate. After evaporation of the solvent, the residue was purified by silica gel column chromatography (eluent; n-hexane:ethyl acetate=3:1) to give 23.4 g of N-[2-cyclohexyloxy-5-(n-valerylamino)-phenyl]methanesulfonamide as a yellow oil.

$^1$H-NMR (CDCl$_3$) ppm: 0.94 (3H, t, J=7Hz), 1.20~2.10 (14H, m), 2.32 (2H, t, J=7 Hz), 2.98 (3H, s), 4.28 (1H, m), 6.81 (1H, brs), 6.88 (1H, d, J=8 Hz), 7.15 (1H, brs), 7.38 (1H, s), 7.59 (1H, d, J=8 Hz)

(5) To 63.5 ml of an acetic acid solution containing 23.4 g of N-[2-cyclohexyloxy-5-(n-valerylamino)-phenyl]methanesulfonamide was added 7.0 g of 60% nitric acid with heating at 90° C. with stirring over a period of 45 minutes, followed by stirring for a further 45 minutes. The reaction solution was cooled back to room temperature, and water was added thereto. The precipitate was collected by filtration, and recrystallized from ethanol to give 13.5 g of N-[2-cyclohexyloxy-4-nitro-5-(n-valerylamino)phenyl]methanesulfonamide as yellow prisms.

m.p. 84°–87° C.

EXAMPLES 2–9

(1) Following an amidation similar to that of Example 1 (4) using N-(5-amino-2-cyclohexyloxyphenyl)methanesulfonamide obtained by the method of Example 1 (1)–(3) as a material, acetic formic anhydride, acetic anhydride, propionyl chloride, n-butyryl chloride, ethoxyoxalyl chloride, n-propoxyoxalyl chloride, methoxycarbonylacetyl chloride and 3-ethoxycarbonylacetyl chloride in place of n-valeryl chloride used in Example 1 (4), there were obtained the amide derivatives shown in Table 1, in which the oily substances were purified by silica gel column chromatography (eluent; n-hexane:ethyl acetate=2:1).

TABLE 1

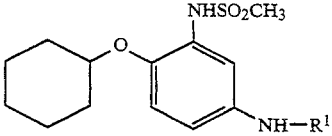

| R$^1$ | m.p. (°C.) |
| --- | --- |
| —CHO | 142~143 |
| —COCH$_3$ | 157~159 |
| —COCH$_2$CH$_3$ | oil; H-NMR(l) |
| —CO(CH$_2$)$_2$CH$_3$ | 129.5~130.5 |
| —COCO$_2$CH$_2$CH$_3$ | 146~147 |
| —COCO$_2$(CH$_2$)$_2$CH$_3$ | 115~116.5 |
| —COCH$_2$CO$_2$CH$_3$ | 112~113.5 |
| —CO(CH$_2$)$_2$CO$_2$CH$_2$CH$_3$ | oil; H-NMR(2) |

$^1$H-NMR(1): 1.22 (3H, t, J=7 Hz), 1.20~2.10 (10H, m), 2.37 (2H, q, J=7 Hz), 2.99 (3H, s), 4.26 (1H, m), 6.82 (1H, brs), 6.85 (1H, d, J=8 Hz), 7.14 (1H, brs), 7.38 (1H, d, J=2 Hz), 7.59 (1H, dd, J=2.8 Hz)

$^1$H-NMR(2): 1.28 (3H, t, J=6 Hz), 1.34~2.10 (10H, m), 2.70 (4H, m), 2.98 (3H, s), 4.18 (2H, t, J=6 Hz), 4.27 (1H, m), 6.82 (1H, brs), 687 (1H, d, J=8 Hz), 7.41 (1H, d, J=2 Hz), 7.52 (1H, dd, J=2.8 Hz)

(2) Following a nitration similar to that of Example 1 (5) using the amide derivatives shown in Table 1, there were obtained the compounds of the present invention shown in Table 2.

TABLE 2

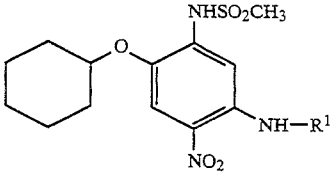

| Example | R$^1$ | m.p. (°C.) |
| --- | --- | --- |
| 2 | —CHO | 158~159 |
| 3 | —COCH$_3$ | 140~142 |
| 4 | —COCH$_2$CH$_3$ | 148~149 |
| 5 | —CO(CH$_2$)$_2$CH$_3$ | 103~104 |
| 6 | —COCO$_2$CH$_2$CH$_3$ | 145~146 |
| 7 | —COCO$_2$(CH$_2$)$_2$CH$_3$ | 176~177 |
| 8 | —COCH$_2$CO$_2$CH$_3$ | 129.5~131 |
| 9 | —CO(CH$_2$)$_2$CO$_2$CH$_2$CH$_3$ | 159.5~161 |

EXAMPLE 10

To 100 ml of a methanol solution containing 5.0 g of N-[5-(n-butyrylamino)-2-cyclohexyloxy-4-nitrophenyl]methanesulfonamide obtained by the method of Example 5 was added 40 ml of a 10% aqueous sodium hydroxide solution at room temperature, followed by stirring for 30 minutes. The reaction solution was made acidic by adding 3N hydrochloric acid, and extracted with ethyl acetate. The organic layer was successively washed with water and a saturated aqueous sodium chloride solution, and dried over anhydrous magnesium chloride. After evaporation of the solvent, the residue was recrystallized from ethanol to give 3.1 g of N-(5-amino-2-cyclohexyloxy-4-nitrophenyl)methanesulfonamide.

m.p. 136°–137° C.

Experiment 1: Test of action on adjuvant arthritis

A test of adjuvant arthritis (therapy) was carried out according to the method of Winder et al as described in Arthritis Rheum., vol. 12, No. 472 (1969).

Seven Lewis strain rats (for each group) were administered subcutaneously 0.7% *Mycobacterium tuberculosis* suspended in liquid paraffin into the left food pad to induce adjuvant arthritis.

15-18 Days after administration of adjuvant, rats with fully developed arthritis were administered orally test drugs 1-11 suspended in 5% gum arabic in an amount of 1 ml per 100 g of body weight (1 mg/kg of dose) once a day for 4 days. On the day after the final administration, the volume of the foot was determined, and the edema inhibition ratio was calculated for the therapeutical effect.

TABLE 3

| Test drug | Edema inhibition ratio (%) |
| --- | --- |
| 1 | 46.5 |
| 2 | 43.1 |
| 3 | 45.7 |
| 4 | 48.5 |
| 5 | 44.2 |
| 6 | 50.9 |
| 7 | 37.2 |
| 8 | 38.0 |
| 9 | 52.8 |
| 10 | 46.7 |

TABLE 3-continued

| Test drug | Edema inhibition ratio (%) |
| --- | --- |
| 11 | 19.7 |

1; The compound of Example 1
2; The compound of Example 2
3; The compound of Example 3
4; The compound of Example 4
5; The compound of Example 5
6; The compound of Example 6
7; The compound of Example 7
8; The compound of Example 8
9; The compound of Example 9
10; The compound of Example 10
11; N-(2-Cyclohexyloxy-4-nitrophenyl)-methanesulfonamide

INDUSTRIAL APPLICABILITY

5-Aminosulfonanilide compounds of the present invention have potent anti-inflammatory, antipyretic, analgesic and anti-allergic actions, and therefore they are useful as anti-inflammatory, antipyretic, analgesic and anti-allergic agents.

We claim:

1. A compound represented by the formula:

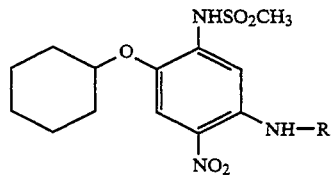

(wherein R is a hydrogen atom, a formyl group, an acetyl group, a propionyl group, an n-butyryl group, an n-valeryl group, an ethoxyoxalyl group, an n-propoxyoxalyl group, a methoxycarbonylacetyl group or a 3-ethoxycarbonylpropionyl group.

* * * * *

UNITED STATES PATENT AND TRADEMARK OFFICE
CERTIFICATE OF CORRECTION

PATENT NO. : 5,374,764
DATED : December 20, 1994
INVENTOR(S) : YOSHIKAWA et al

It is certified that error appears in the above-indentified patent and that said Letters Patent is hereby corrected as shown below:

Col. 3, line 16, "sulfideammonium" should read --sulfide-ammonium--.

Col. 6, line 23, "687" should read --6.87--.

Col. 7, line 20, insert a new paragraph, --Results are shown in Table 3.--.

Signed and Sealed this

Twenty-ninth Day of August, 1995

Attest:

BRUCE LEHMAN

Attesting Officer     Commissioner of Patents and Trademarks